United States Patent [19]

Hoene

[11] 4,343,954

[45] Aug. 10, 1982

[54] FORMALDEHYDE PROCESS

[75] Inventor: David J. Hoene, Wilmington, Del.

[73] Assignee: E. I. Du Pont de Nemours and Company, Wilmington, Del.

[21] Appl. No.: 258,382

[22] Filed: Apr. 28, 1981

[51] Int. Cl.³ .......................................... C07C 47/052
[52] U.S. Cl. .................................. 568/473; 568/472; 568/474
[58] Field of Search ........................ 568/473, 472, 474

[56] References Cited

U.S. PATENT DOCUMENTS

| | | | |
|---|---|---|---|
| 2,462,413 | 2/1949 | Meath | 260/603 |
| 2,519,788 | 8/1950 | Payne | 260/603 |
| 3,959,383 | 5/1976 | Northeimer | 260/603 C |
| 4,119,673 | 10/1978 | Aicher et al. | 260/603 C |

Primary Examiner—Werren B. Lone

[57] ABSTRACT

A process for converting methanol to formaldehyde wherein methanol along with a stream containing air, water, methanol and formaldehyde is fed to a primary reactor 5 containing a silver catalyst maintained at from 630° to 650° C. The effluent from the primary reactor 5 is cooled and fed along with a stream containing air, water, methanol and formaldehyde to a secondary reactor 9 containing a metal oxide catalyst, such as iron oxide-molybdenum oxide. The secondary reactor 9 is maintained at from 325° to 400° C. The product from the secondary reactor is fed to an absorber 11 which is cross connected top and bottom with a stripper 13. Water is fed to the absorber to absorb formaldehyde and the product solution of formaldehyde and water is removed from the absorber. Air is fed to the stripper and the effluent from the stripper which contains air, water, methanol and formaldehyde is fed to both the primary reactor 5 and the secondary reactor 9.

4 Claims, 1 Drawing Figure

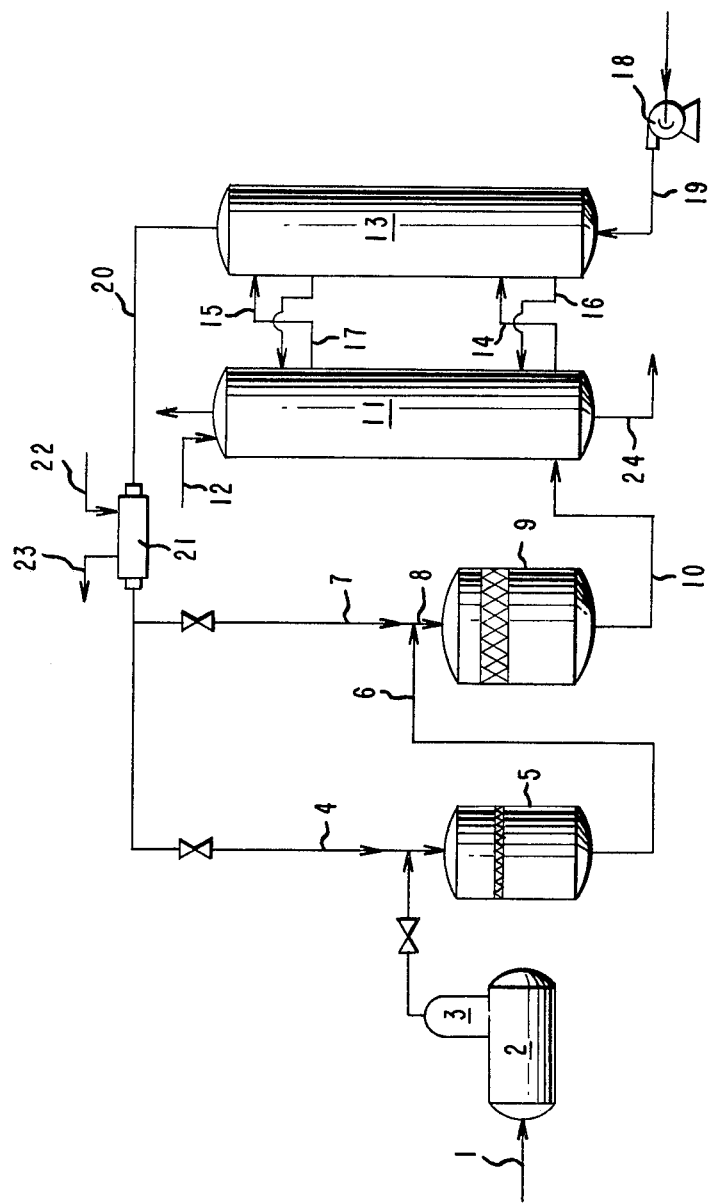

FORMALDEHYDE PROCESS

BACKGROUND OF THE INVENTION

1. Field of the Invention

The present invention relates to a process for the catalytic conversion of methanol to formaldehyde. In particular, the present invention relates to a process for preparing formaldehyde from methanol using an adiabatic, silver catalyzed primary reactor and an adiabatic, metal oxide catalyzed secondary reactor wherein the air used in the reaction is also used to strip methanol and water from the product.

2. Prior Art

There are two commercially accepted processes for converting methanol to formaldehyde. The first utilizes a silver catalyst and operates in an oxygen lean atmosphere. The second utilizes a metal oxide catalyst and operates in a methanol lean atmosphere. The first process involves passing a mixture of methanol vapor and air over a fixed bed catalyst at approximately atmospheric pressure and absorbing the product gases in water. The mechanism is believed to be a combination of two reactions involving the dehydrogenation and oxidation of methanol:

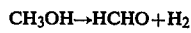

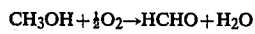

Silver-catalyzed processes for making formaldehyde from methanol can be characterized according to the number of catalytic stages used to effect the conversion. Single stage operation is quite widely used but suffers from the disadvantage that rather high amounts of unconverted methanol are contained in the product emerging from the catalyst bed. This phenomenon is customarily referred to as methanol leakage. Since for many applications methanol is an undesirable contaminant, it must be separated from the formaldehyde solution. This entails a substantial investment in distillation facilities and energy to carry out such separations. It is usually necessary that the methanol content of the product be no greater than 2% by weight.

One way of eliminating the need for facilities to distill off methanol is to use two catalytic stages with interstage cooling. A basic two-stage process for this type is disclosed in Meath U.S. Pat. No. 2,462,413. In Northeimer U.S. Pat. No. 3,959,383 in improvement on the Meath process is disclosed by which even lower amounts of methanol in the product can be obtained.

In addition to the above-described dual silver two-stage processes, other two-stage processes have been described in the art. U.S. Pat. No. 2,519,788 to Payne describes a process for converting methanol to formaldehyde using an adiabatic first stage reactor containing a silver catalyst and an isothermal second stage reactor containing a metal oxide catalyst.

U.S. Pat. No. 4,119,673 to Aicher et al discloses a process utilizing a single stage conversion of methanol to formaldehyde over silver catalyst wherein the air used in the reaction enters the reaction system through a stripping column.

SUMMARY OF THE INVENTION

The process of the present invention uses an inexpensive, adiabatic, secondary reactor containing a highly selective iron oxide-molybdenum oxide catalyst in series with an adiabatic secondary reactor containing silver for conversion of methanol to formaldehyde. In the process, low temperature, normally wasted, energy from the reaction gas absorber is used in stripping excess methanol and water from the absorber bottoms with reaction air. Water in the reaction air provides a heat sink for controlling the temperature in the adiabatic reactors along with improving catalyst selectivity. Recovery of excess methanol and water from the absorber bottoms allows the reactors to operate at lower than normal conversions thereby improving the yield while still producing a high strength formaldehyde product.

BRIEF DESCRIPTION OF THE DRAWING

The drawing is a schematic flow diagram illustrating the process of the present invention.

DETAILED DESCRIPTION OF THE DRAWING

A stream of methanol 1 is fed to a methanol vaporizer 2 and superheater 3 where the methanol is vaporized and heated to from 160° to 180° C. and subsequently mixed with recycle line 4. Recycle line 4 contains 45 to 55 volume % nitrogen, 12 to 14 volume % oxygen, 1.6 to 2.0 volume % methanol, from 27 to 33 volume % water and from 4.0 to 4.8 volume % formaldehyde at from 160° to 180° C. The combined streams are fed to primary reactor 5 containing a silver catalyst. Since the oxidation of methanol to formaldehyde is exothermic, the temperature is controlled partly by the air to methanol ratio and partly by the quenching effect of the recycled non-reactive gases nitrogen and water. In the present process invention oxygen is present in an amount sufficient to give a methanol conversion of 80 to 90% and preferably 84 to 90%. With this high a conversion, a very high catalyst bed temperature ordinarily would occur. However, in the process of the present invention this high a conversion can be obtained while maintaining the catalyst bed under 660° C. and generally in range of from 630° to 650°C. Generally the pressure in the primary reactor will be from 5 to 15 psig.

In addition to a conventional silver catalyst a mixed silver-gold catalyst as described in U.S. Pat. No. 4,167,527 or Ser. No. 871,596 filed Jan. 23, 1978 can be used. As described therein, the silver-gold catalyst contains about 20–95 atomic % silver and 80 to 5 atomic % gold preferably about 40–60 atomic & gold. Thus in the present process the first stage catalyst is about 20–100 atomic % silver and 0 to about 80 atomic % gold.

The reaction gases in primary reactor 5 are cooled to 200° to 240° C. to reduce formaldehyde decomposition and are fed through line 6 to be mixed with recycle gases in line 7, maintained at from 160° to 180° C., so as to maintain the feed temperature of the gases in line 8 at from 190° to 210° C. The ratio of oxygen to methanol by volume in line 8 is maintained at from 2.0:1 to 2.2:1. Thus the ratio of flow rate of recycle gas in line 7 to the flow rate of gas in line 6 is from 0.8:1 to 1.0:1. Gases in line 8 are fed to secondary reactor 9 which contains a metal oxide catalyst. The above-described amount of oxygen contained in the inlet gases to secondary reactor 9 provides oxygen in excess of that required to convert methanol unconverted to formaldehyde in primary reactor 5 to formaldehyde and byproducts.

Metal oxide catalysts for the catalytic oxidation of methanol to formaldehyde are well known in the art. Any of these can be used in the second state of the present invention. Illustrative metal oxides are the oxides of vanadium, molybdenum, magnesium and manganese used alone, together or with oxides of metals such as iron, cobalt, chromium and bismuth. A preferred catalyst is an iron oxide-molybdenum oxide catalyst with or without a minor quantity of cobalt molybdate. This latter catalyst can be prepared as described in U.S. Pat. No. 3,855,153, issued Dec. 17, 1974, to G. M. Chang. Unmodified iron-molybdate catalysts are described in U.S. Pat. Nos. 1,913,405; 2,812;309; 3,152,997; 3,408,309; 3,420,783; and 3,716,497. A useful bismuth phosphomolybdate catalyst is described in U.S. Pat. No. 3,415,886. Bismuth molybdate as a catalyst for the oxidation of methanol is described in U.S. Pat. No. 2,491,695. By only having about 10-20 volume percent (preferably 10-15) unreacted methanol from the first reactor fed to the secondary reactor, the conversion of this remaining methanol is carried out without external cooling of the secondary reactor and without the catalyst bed temperature rising to a temperature where the catalyst is deactivated. As is well known, a metal oxide catalyst as used in the manufacture of formaldehyde cannot tolerate as high a temperature as a silver catalyst. Thus, the maximum catalyst bed temperature in the secondary reactor is about 400° C., with a temperature usually in the range of about 300°-400° C. while obtaining a methanol conversion of about 10 percent with a formaldehyde yield of about 90%. The principle by-products are $CO_2$ (about 9% of the methanol converted) and CO (about 1% of the methanol converted).

The reaction gases from secondary reactor 9 are fed through line 10 to absorber 11. Water is fed to absorber 11 through line 12 to absorb the product formaldehyde. Generally the water will be at from 10° to 30° C. and is fed at a rate to provide a 52 to 59 wt % formaldehyde in water solution as product. The bottoms from absorber 11 are recycled to the bottom of the stripper 13 via lines 14 & 16. A high side stream from absorber 11 is recycled to the top half of the stripper 13 via lines 15 & 17. Air is fed by compressor 18 through line 19 to stripper 13. Alternately air can be pulled through the stripper by installing the blower in line 20). Air saturated with water vapor methanol and formaldehyde is fed from stripper 13 via line 20 to a superheater 21 and then on to primary reactor 5 and secondary reactor 9. Superheater 21 heats the gases passing therethrough to from 160° to 180° C. Product formaldehyde is removed in line 24 as a stream which contains 52 to 59 wt. % formaldehyde.

Due to the recycle stream 20, the process can be operated at an overall conversion of methanol of about 98% with high yield of formaldehyde of 88 to 90%.

DESCRIPTION OF THE PREFERRED EMBODIMENT

The apparatus depicted in the Drawing is used in this example.

Superheated methanol vapor is mixed with recycle line 4 at a rate of 15,238 pounds per hour (6,926 Kg/hr). Line 4 contains methanol vapor [687 lbs/hr (312 Kg/hr)], formaldehyde vapor [1,544 lbs/hr (706 Kg/hr)], water vapor [6,245 lbs/hr (2,839 Kg/hr)], oxygen [4,992 lbs/hr (2,269 Kg/hr)], and nitrogen [16,572 lbs/hr (7,533 Kg/hr)], under a pressure of 10 psig (69 kPa gauge). The combined streams are fed to reactor 5. Reactor 5 is operated at 10 psig (69 kPA gauge) and 640° C. Reactor 5 contains a conventional silver methanol oxidation/dehydrogenation catalyst. The reaction product comprising 2,389 lbs/hr (1,086 Kg/hr) methanol, 13,102 lbs/hr (5,955 Kg/hr) formaldehyde, 11,011 lbs/hr (5,005 Kg/hr) water, 220 lbs/hr (100 Kg/hr) oxygen, 16,572 lbs/hr (7,533 Kg/hr) nitrogen, 316 lbs/hr (144 Kg/hr) hydrogen, 1,489 (677 Kg/hr) $CO_2$ and 118 lbs/hr (54 Kg/hr) CO is combined with line 7 comprising 910 lbs/hr (414 Kg/hr) methanol, 2,061 lbs/hr (937 Kg/hr) formaldehyde, 8,267 lbs/hr (3,758 Kg/hr) water, 6,608 lbs/hr (3,004 Kg/hr) oxygen, and 21,936 lbs/hr (9,971 Kg/hr) nitrogen and fed to secondary reactor 9. Secondary reactor 9 contains a conventional iron oxide-molybdenum oxide catalyst and is operated at 350° C. and 5 psig (34 kPa). The effluent from secondary reactor 9 contains 1,980 lbs/hr (900 Kg/hr) methanol, 16,240 lbs/hr (7,382 Kg/hr) formaldehyde, 20,088 lbs/hr (9,131 Kg/hr) water, 6,108 lbs/hr (2,776 Kg/hr) oxygen, 38,508 lbs/hr (17,503 Kg/hr) nitrogen, 316 lbs/hr (144 Kg/hr) hydrogen, 1,670 lbs/hr (759 Kg/hr) carbon dioxide, and 129 lbs/hr (59 Kg/hr) carbon monoxide, and is fed to absorber 11. Water at ambient temperature is fed to absorber 11 via line 12 at a rate of 6,836 lbs/hr (3,107 Kg/hr). Air is blown into a stripper 13 via line 19 at a rate of 11,600 lbs/hr (5,273 Kg/hr) oxygen and 38,508 lbs/hr (17,504 Kg/hr) nitrogen. Off gases comprising 76 lbs/hr (35 Kg/hr) methanol, 125 lbs/hr (57 Kg/hr) formaldehyde, 1,634 lbs/hr (743 Kg/hr) water, 5,889 lbs/hr (2,677 Kg/hr) oxygen, 38,508 lbs/hr (17,504 Kg/hr) nitrogen, 316 lbs/hr (144 Kg/hr) hydrogen, 1,670 lbs/hr (759 Kg/hr) carbon dioxide and 129 lbs/hr (59 Kg/hr) carbon monoxide. The product formaldehyde is removed as stream 24 which contains 12,500 lbs/hr (5,682 Kg/hr) formaldehyde, 10,778 lbs/hr (4,899 Kg/hr) water and 307 lbs/hr (140 Kg/hr) methanol. An overhead recycle stream is removed from stripper 13 heated to 165° C. and recycled to primary reactor 5 and secondary reactor 9 in the amounts reported above.

I claim:

1. A process comprising feeding the effluent from a primary reactor for converting methanol to formaldehyde along with air and recycled methanol, water and formaldehyde to an adiabatic seconary reator utilizing a metal oxide catalyst comprising an oxide or oxides of vanadium, iron, molybdenum, magnesium or manganese, maintaining said secondary reactor at from 300° to 400° C., to provide an overall conversion of 94 to 98%, feeding the effluent from said secondary reactor to an absorber, feeding water to said absorber to absorb formaldehyde, feeding air to a stripper, recycling formaldehyde solution from the bottom section of said absorber to the bottom section of said stripper, recycling formaldehyde solution from the top section of said absorber to the top section of said stripper, recycling air saturated with water, methanol and formaldehyde from said stripper to said secondary reactor, and removing product formaldehyde and water solution from said absorber.

2. The process of claim 1 wherein methanol is mixed with part of air saturated with methanol and formaldehyde from the stripper and fed to the primary reactor which utilizes a silver catalyst and is operated at a temperature of from 630° to 650° C. to provide a conversion of methanol of from 80 to 90%.

3. The process of claim 2 wherein the primary reactor is operated at a conversion of methanol of from 84 to 90%.

4. The process of claim 3 wherein the metal oxide catalyst consists essentially of iron oxide and molybdenum oxide.

* * * * *